(12) United States Patent
Bailey et al.

(10) Patent No.: US 6,210,679 B1
(45) Date of Patent: Apr. 3, 2001

(54) METHOD FOR ISOLATION OF CAFFEINE-FREE CATECHINS FROM GREEN TEA

(75) Inventors: David T. Bailey, Boulder; Ralph L. Yuhasz, Denver, both of CO (US); BoLin Zheng, Wayne, NJ (US)

(73) Assignee: Hauser, Inc., Boulder, CO (US)

( * ) Notice: Subject to any disclaimer, the term of this patent is extended or adjusted under 35 U.S.C. 154(b) by 0 days.

(21) Appl. No.: 09/226,477

(22) Filed: Jan. 7, 1999

(51) Int. Cl.[7] .............................. A61K 35/78; A23F 3/34; A23F 3/36
(52) U.S. Cl. .................... 424/195.1; 426/425; 426/427; 426/435; 549/399; 514/456
(58) Field of Search .................... 424/195.1; 426/425, 426/427, 435; 549/399; 514/456

(56) References Cited

U.S. PATENT DOCUMENTS

| | | | |
|---|---|---|---|
| 4,613,672 | * 9/1986 | Hara | 549/399 |
| 4,806,379 | 2/1989 | Goers et al. | 426/650 |
| 5,021,253 | 6/1991 | Dawson-Ekeland et al. | 426/422 |
| 5,043,100 | 8/1991 | Chang et al. | 252/398 |
| 5,391,568 | 2/1995 | Chung . | |
| 5,804,567 | 9/1998 | Cheng et al. . | |

FOREIGN PATENT DOCUMENTS

| | | |
|---|---|---|
| 1067359 | * 12/1992 | (CN) . |
| 0 167 399 | 1/1986 | (EP) . |
| 0 547 370 A2 | 6/1993 | (EP) . |
| 51104096 | * 9/1976 | (JP) . |
| 362061569 | * 3/1987 | (JP) . |
| 04077424 | * 3/1992 | (JP) . |
| 10067771 | * 3/1998 | (JP) . |
| WO 96/28178 | 9/1996 | (WO) . |

OTHER PUBLICATIONS

Amarowicz et al. J. Food Lipids. vol. 2, No. 1, pp. 47–56, abstract enclosed, 1995.*

Tamagawa et al. J. Jap. Soc. Food Sci. Tech. vol. 44, No. 7, pp. 512–515, abstract enclosed, 1995.*

"Actiquench® GTP 20," Active Organics, (May 1997).

"Prophylactic Functions of Tea Polyphenols," Food Research Laboratories, Mitsui Norin Co., Ltd. (Dec. 1993).

"Tea and Cancer," Chung S. Yang, Zhi–Yuan Wang, *Journal of the National Cancer Institute*, 85:1038–1049, Jul. 7, 1993.

"Separation of the Components in Black Tea Infusion by Chromatography on Toyopearl," Tetsuo Ozawa, *Agric. Biol. Chem.*, 46(4):1079–1081 (1982).

"Greenselect™, A Caffeine–free, standardized extract from green tea leaves," Indena.

"Green Tea (*Camellia sinensis* (L.) O. Kuntze)," Planextrakt GmbH Et Co KG.

"Polyphenon60™ (Green Tea Extract)," Mitsui Norin Co., Ltd.

* cited by examiner

*Primary Examiner*—Christopher R. Tate
(74) *Attorney, Agent, or Firm*—Steven C. Peterson; Sarah S. O'Rourke; Hogan & Hartson, LLP

(57) ABSTRACT

The process of the present invention relates to the isolation and purification of caffeine-free mixtures catechins from various different biomass sources, preferably from green tea leaves. More particularly, the present invention relates to a four-step process whereby highly pure, caffeine-free EGCG is isolated in high yields. These catechins may be used in pharmaceutical, nutraceutical and cosmetic products.

30 Claims, 4 Drawing Sheets

(−)-EPICATECHIN (EC)

(−)-EPIGALLOCATECHIN (EGC)

(−)-EPICATECHIN-3-GALLATE (ECG)

(−)-EPIGALLOCATECHIN-3-GALLATE (EGCG)

METHOD FOR ISOLATION OF CAFFEINE-FREE CATECHINS FROM GREEN TEA

CROSS-REFERENCE TO OTHER APPLICATIONS

This patent application references Disclosure Document No. 436778, filed May 22, 1998, entitled Method for the Purification of Catechins and Caffeine from Green Tea Extract Solids Using Chromatography on Polyamide.

BACKGROUND OF THE INVENTION

1. Field of the Invention

The present invention relates to a process for the isolation and purification of caffeine-free catechins from a number of different biomass sources. More particularly, the present invention relates to a four-step process whereby highly pure, caffeine-free EGCG is isolated and purified in high yields from plant materials such as green tea leaves.

2. Description of the State of Art

Commercial green tea is made by steaming or drying fresh tea leaves at elevated temperatures. Its chemical composition is similar to that of fresh tea leaves. Green tea contains polyphenols, which include flavanols, flavandiols, flavonoids, and phenolic acids; these compounds may account for up to 30% of the dry weight. Most of the green tea polyphenols are flavanols, commonly known as catechins. Some major green tea catechins are (−)-epigallocatechin-3-gallate (EGCG), (−)-epigallocatechin (EGC), (−)-epicatechin-3-gallate (ECG), (−)-epicatechin (EC), (+)-gallocatechin, and (+)-catechin. The chemical structures of some of these compounds are shown in FIG. 1. Caffeine, theobromine and theophylline, the principal alkaloids, account for about 4% of the dry weight.

Many laboratory studies have demonstrated inhibitory effects of tea preparations and tea polyphenols against tumor formation and growth. This inhibitory activity is believed to be mainly due to the antioxidative and possible antiproliferative effects of polyphenolic compounds, and in particular the major catechins EGCG, EGC, ECG and EC in green tea. The major constituent and possibly the most powerful of these catechins is EGCG. These catechins may also inhibit ,carcinogenesis by blocking the endogenous formation of N-nitroso compounds, suppressing the activation of carcinogens, and trapping of genotoxic agents (Yang, C. and Wang, Z.-Y., *J. National Cancer Institute* 85:1038 (1993)).

Investigators have tested EGCG on cancerous human and mouse cells of the skin, lymph system, and prostate, and on normal human skin cells. In vitro, EGCG resulted in the induction of apoptosis, or programmed cell death, in cancer cells, but not in normal cells (*Journal of the National Cancer Institute*, 89, (1997)). In addition, it was noted that EGCG did not cause necrosis of healthy cells. This selectivity, if it can be observed in vivo at desirable doses, will be of great therapeutic importance, since a vast variety of chemotherapeutic agents currently used in cancer therapy are thought to kill cells by mechanisms other than apoptosis. Thus, green tea, and in particular its major component, EGCG, appear to be ideal agents for chemotherapy because they appear to have little or no known side effects.

Disadvantages to drinking green tea for health benefits includes the fact that individuals may need to consume large quantities of tea in order to receive even small therapeutic amounts of catechins. Further, brewed tea contains caffeine, which is known to have undesired effects on the cardiovascular system as well as a mutagenic effect.

Therefore, there is a need to isolate a caffeine-free composition of green tea catechins having a known amount of EGCG.

Antioxidants have been used in cosmetics, for example sun screens, to prevent or to lessen the amount of tissue damage due to free radicals. Free radical damage is often initiated by environmental factors such as exposure to UV light, which can increase the number of free radicals in the skin, which in turn can damage DNA. Free radical damage has been linked to the aging process in addition to chronic degenerative diseases including heart disease, arthritis, and cancer. Natural defense systems in biological systems react directly with the free radicals to prevent damage to tissue. Unfortunately, the body's antioxidant defense system is often not efficient enough to counter free radical production rates during periods of prolonged exposure to environmental factors. Vitamin E has been shown to assist in the repair of lipid peroxides formed by free radicals but does not prevent them from forming. Melatonin has been shown to protect against the effects of hydroxide radicals, but not oxygen radicals. Green tea catechins have been shown to not only prevent against lipid peroxidation but also scavenge both oxygen and hydroxide radicals.

In addition, antioxidants are widely used in pharmaceuticals, cosmetics, essential oils and plastics for food packaging. Butylated hydroxy anisole (BHA), a synthetic antioxidant, was formerly the most widely used antioxidant worldwide. However, because of its possible carcinogenicity, the use of BHA is banned or restricted in many countries. Tocopherol (Vitamin E) is an antioxidant from natural sources. Tocopherol is not carcinogenic, however, its lipophilic property limits its wider use. Therefore, there is a need for effective, safe, and natural antioxidants. Tea catechins are known to have antioxidative property. The antioxidative effects of four catechins have been tested in lard, and their antioxidative activity increased in the following order: EC<ECG<EGC<EGCG.

Several methods have been described in the prior art for producing decaffeinated green tea or for isolating catechins from green tea. U.S. Pat. No. 5,043,100 (Chang, et al.) describes vacuum steam distillation of alcohol extracts of green tea. However, Chang et al. do not characterize the compositions of the distillates, nor do they indicate whether or not caffeine has been eliminated from the distillates.

U.S. Pat. No. 4,613,672 (Hara) describes a process for the production of a mixture of tea catechins comprising EC, EGC, ECG and EGCG by extracting tea leaves with hot water or an aqueous alcoholic solution, washing this extract with chloroform to remove caffeine, extracting catechins in the aqueous layer into an organic solvent and distilling the organic phase. This method, which uses a toxic solvent in the extraction process, does not provide for the isolation of EGCG in highly pure form from the mixture of catechins.

EP 547370(B1) (So) describes a method for preparing an antioxidant which involves extracting tea leaves with water and then fractionating the extract by means of liquid chromatography using water as the eluent. However, So does not indicate whether or not caffeine has been removed from the antioxidants and does not give the composition or purity of the antioxidant.

WO 96/28178 (Bombardelli, et al.) describes a method for the preparation of decaffeinated mixture of polyphenols by washing green tea extracts with chlorinated solvents. These mixtures comprise 50–65% EGCG, 13–20% ECG, 2–4% EC and 1.5–35 EGC, and this method does not provide for the isolation of EGCG in a highly pure form. In addition, this method uses a toxic solvent in the extraction process.

The above examples describe some of processes that currently exist for extracting and purifying catechins from various plant materials. However, in addition to some of the disadvantages already discussed, many of the disclosed processes are also not easily scaled up to an efficient commercial process where disposal considerations of various solvents play an important role in the overall feasibility of the process.

A further disadvantage of the processes disclosed in the prior art is the inability to achieve a high concentration and purity level of EGCG, and in particular, caffeine-free EGCG of high purity. Rather, the above processes result in mixtures of catechins having various concentrations of EGCG.

There is still a need, therefore, for an efficient process and procedure for isolating and purifying caffeine-free catechins of desired compositions for uses in pharmaceuticals, nutraceuticals and cosmetics which is cost-effective, scalable, and which does not require the use of toxic solvents. Further, there exists a need for a process for isolating and purifying a caffeine-free catechin mixture having a desired concentration of EGCG.

SUMMARY OF THE INVENTION

Accordingly, it is an object of the present invention to provide a simplified method for the isolation and purification of a range of desired caffeine-free catechin compositions and purities in high yields. More specifically the method of the present invention yields caffeine-free mixtures of catechins in a range of purity of 30–95% and caffeine-free EGCG in a range of purity of 15–88%.

An additional object of the present invention is further directed to formulations comprising caffeine-free catechins isolated by the method of the invention.

A further object of the present invention is also directed to the use of EGCG in therapeutics comprising administering an effective amount of highly pure, caffeine-free EGCG isolated by the method of the present invention.

Additional objects, advantages and novel features of this invention shall be set forth in part in the description that follows, and in part will become apparent to those skilled in the art upon examination of the following specification or may be learned by the practice of the invention. The objects and advantages of the invention may be realized and attained by means of the instrumentalities, combinations, and methods particularly pointed out in the appended claims.

To achieve the foregoing and other objects and in accordance with the purposes of the present invention, as embodied and broadly described therein, the method of this invention comprises contacting a plant material with a solvent thereby forming a crude extract, loading the crude extract onto a first column containing an adsorbent for specifically adsorbing catechins, removing extraneous materials by washing the adsorbent with specific solvents, and desorbing the catechins from the adsorbent using 100% food grade (95%) ethanol, wherein the fractions eluting from the column with 100% food grade ethanol contain caffeine-free mixed catechins comprise about 25–40% EGCG and are about 70–80% pure in catechins. Alternatively, the extraneous materials may be removed by washing the adsorbent with water containing between 0–10% ethanol, the catechins may then be desorbed from the adsorbent by eluting with 55% ethanol, and small fractions are collected and pooled based on the composition of the fractions, thus isolating a caffeine-free catechin mixture comprising about 60–75% EGCG, wherein the mixture has a purity of about 78–82% in catechins. If a substantially pure caffeine-free EGCG product having a higher purity level is desired, selected eluent from the 55% ethanol elution is collected as a single fraction and then this mixture of caffeine-free catechins is further loaded onto a second column containing a second adsorbent specific for catechins and eluted with 5–12% ethanol, thus yielding a substantially pure caffeine-free EGCG, wherein the substantially pure caffeine-free EGCG comprises about 85–95% EGCG. If ahighly pure caffeine-free EGCG product is desired, the eluent discussed above comprising the substantially pure caffeine-free EGCG may be further loaded onto a solvent exchange column, wherein methanol is used to elute the substantially pure EGCG, and then and the substantially pure caffeine-free EGCG is crystallized to yield highly pure, caffeine-free EGCG product comprising about 98% EGCG having a purity of about 95%.

BRIEF DESCRIPTION OF THE DRAWINGS

The accompanying drawings, which are incorporated in and form a part of the specification, illustrate the preferred embodiments of the present invention, and together with the descriptions serve to explain the principles of the invention.

DETAILED DESCRIPTION OF THE PREFERRED EMBODIMENT

Figure 1:
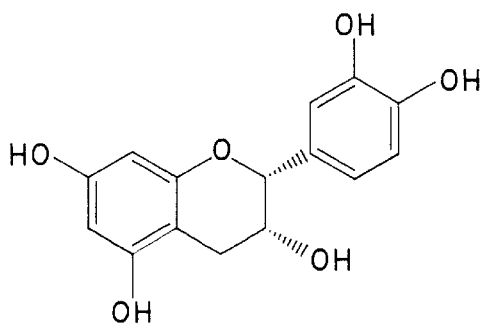
FIG. 1 shows the structures of the major green tea catechins epicatechin (EC), epicatechin gallate (ECG), epigallocatechin (EGC) and epigallocatechin gallate (EGCG).
Figure 1:
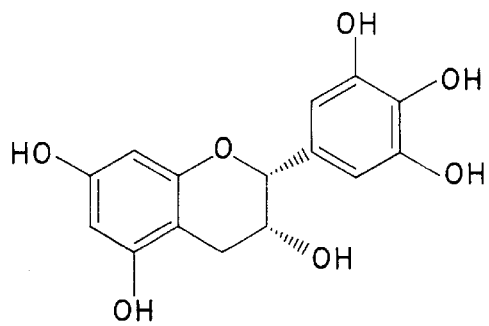
Figure 1:
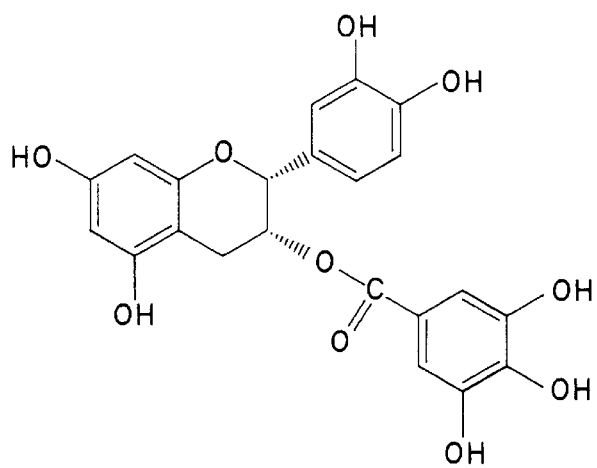
Figure 1:
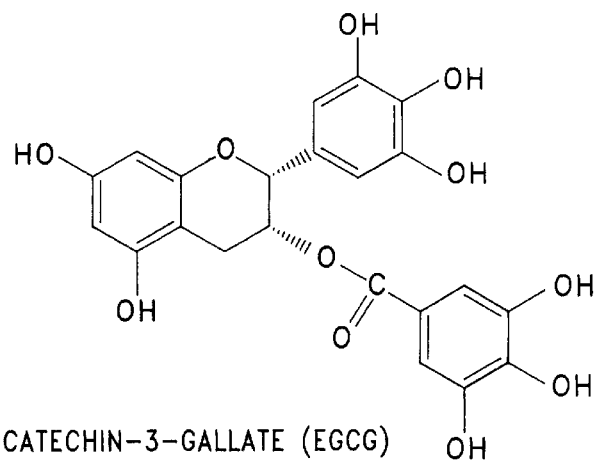

In general the present invention relates to a high yield process for the isolation and purification of caffeine-free catechins from a particular plant material, including but not limited to, partially purified catechins such as those shown in FIG. 1. Specifically, the invention relates to a high yield process for the isolation of caffeine-free catechins having various purity levels of EGCG.

The preferred embodiment of the present invention for the isolation and purification of high purity, caffeine-free EGCG is a four step process and is described in detail below. Prior to the first step of the process of the present invention, plant material that contains catechins is prepared by contacting the plant material with a solvent, thus resulting in a crude extract containing a mixture of compounds that includes catechin compounds and extraneous materials such as caffeine. The first step of the purification and isolation method involves adsorbing the catechin compounds in the crude extract onto a reversed phase matrix, removal of extraneous materials, specific desorption of certain catechins from the matrix using specific eluents, and then evaporating selected fractions to yield a caffeine-free mixture of catechins. The second step involves adsorbing the caffeine-free mixture of catechins onto a second reversed phase matrix followed by the specific desorption of catechins using specific eluents, and then evaporating selected fractions to afford caffeine-free mixture of catechins of substantial purity, the majority of the catechin mixture comprising EGCG. The third step of the process involves passing the substantially pure, caffeine-free mixture of catechins through a solvent exchange column to exchange any residual water with methanol. The fourth and final step involves crystallization of the substantially pure, caffeine-free mixture of catechins to achieve a final, highly pure composition comprising about 98% EGCG.

This invention includes a process for the extraction, isolation and purification of catechins from plant materials or biomasses that contain catechins, such as green tea leaves (*Camellia sinensis*). Prior to first step in the process of the present invention, catechins are extracted from plant material. The degree of comminution of the plant material should provide sufficient particulate surface area for the first solvent to contact. The skilled person in this art will recognize that a variety of extraction methods are available in the literature, such as percolation, vat extraction, countercurrent extraction, etc. The particular method of extraction employed is not essential to the process of the present invention.

In a preferred embodiment, extraction process is accomplished by placing the plant material in a solvent such as water or ethanol at a temperature between room temperature and 100° C., with 55–60° C. being preferred. The amount of plant material to solvent mixture used in the extraction process varies between 1:10 to 1:30 on a gram to milliliter basis, with 1:30 being preferred.

The catechins and some of the extraneous materials, for example caffeine, that are contained in the comminuted plant material are soluble in the first solvent used. Thus, the first solvent, the catechins and some of the extraneous materials form the crude extract. The crude extract may be filtered at this point, however it is not necessary to filter the crude extract prior to performing the first step of the purification process. If a solvent other than water is used as the extraction solvent, the extraction solvent is partially or completely evaporated and the concentrated extract is diluted with water to form a solution with no more than 5% ethanol prior to the first step of the purification process.

After completion of the formation of the crude extract, the first step, the separation of the catechins, begins. Since the crude extract contains not only the desired catechins but also extraneous materials that are soluble in the first solvent of the crude extract, it is desirable to recover the catechins with as little extraneous material as possible. In a preferred embodiment, the first step of the purification process isolates a mixture of catechins essentially free of caffeine. Preferably, the mixtures comprise less than about 1% caffeine, and most preferably, the mixtures comprise less than about 0.1% caffeine. To recover the caffeine-free mixed catechins, a water diluted crude extract is loaded onto a first column having an absorbent specific for catechins, preferably a reversed phase matrix. In the first step the preferred adsorbent is a polyamide, including but not limited to, Polyamide CC6, manufactured by Machery-Nagel (Germany).

Figure 2:
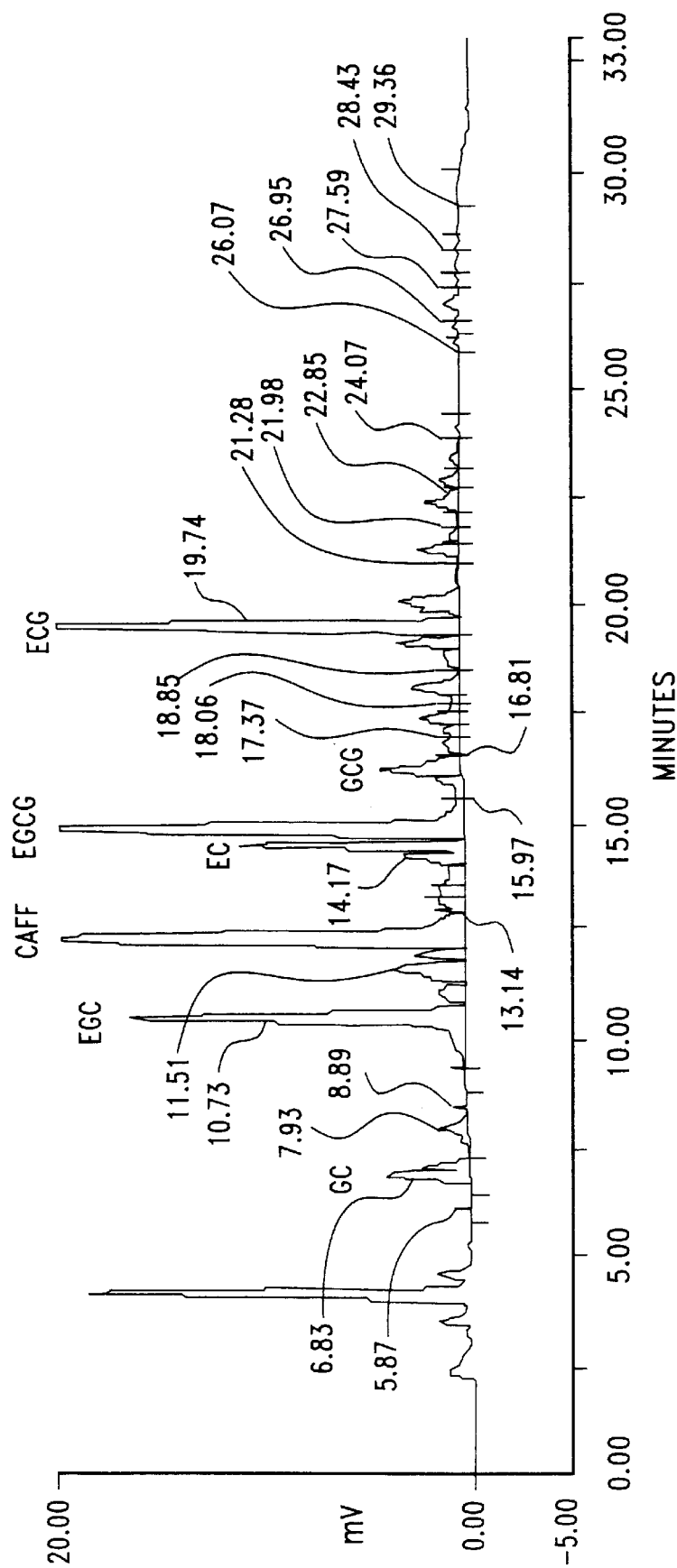
FIG. 2 shows a typical chromatogram of green tea extract prior to purification.

Subsequent to loading the crude extract onto the matrix, extraneous materials such as caffeine, which have little or no affinity for the adsorbent, are specifically washed from the column matrix using water, preferably with 4–5 column volumes of water. This wash is followed by a second wash of water comprising a 10% aqueous solution of food grade (95%) ethanol/water. Optionally, type 3C ethanol (95% ethanol/5% isopropanol), which is more cost-effective, may be used in this case at a concentration of 9.5% 3C ethanol/water. Preferably, 6–8 column volumes of the ethanol/water are used in the second wash. Ethanol in the second water wash removes some undesired catechins such as GC, EGC and a substantial portion of EC from the column. Finally, the remaining catechins are desorbed from the matrix using 100% food grade (95%) ethanol or 100% 3C ethanol. FIG. 2 illustrates a typical chromatogram for green tea leaves extract prior to step 1 and shows the retention times for various components of green tea leaves, including the catechins EGC, EC, EGCG and ECG, and extraneous material such as caffeine. Typical concentrations of these components in green tea leaves are 18.2% EGC, 4.1% EC, 14.9% EGCG, 3.9% ECG, 4% miscellaneous catechins, and 5.8% caffeine. The peak for caffeine appears at approximately 12 minutes. A chromatogram for a caffeine-free catechin mixture isolated after the 100% food grade ethanol or 3C ethanol elution in step 1 indicated that the catechin mixture was essentially free of caffeine as demonstrated by the fact that the caffeine peak was less than 1% of the total mixture. The composition of the caffeine-free catechin mixture isolated from step 1 in this embodiment comprises approximately 75% total catechins and 30% EGCG. This caffeine-free catechin mixture is desirable for use in nutraceuticals.

In an alternative embodiment of step 1, if a mixture of catechins of higher purity is desired, the step 1 is modified as follows. After removal of extraneous material with water followed by 10% ethanol/water, the remaining catechins are eluted with 55% food grade ethanol/water or 51% 3C ethanol/water. In this embodiment, small fractions, for example 0.2 column volume fractions, are collected, and the fractions pooled based on the compositions of the fractions as determined by HPLC. In this embodiment, fractions may be combined in a manner such that a caffeine-free mixture of catechins comprising 60–75% EGCG and having a purity of 78–82% catechins may be isolated. Such a composition is desirable for use in cosmetic products. In an alternative embodiment, all of the fractions from the elution with 55% food grade ethanol may be combined for use in the second step of the process of the present invention.

Figure 3:
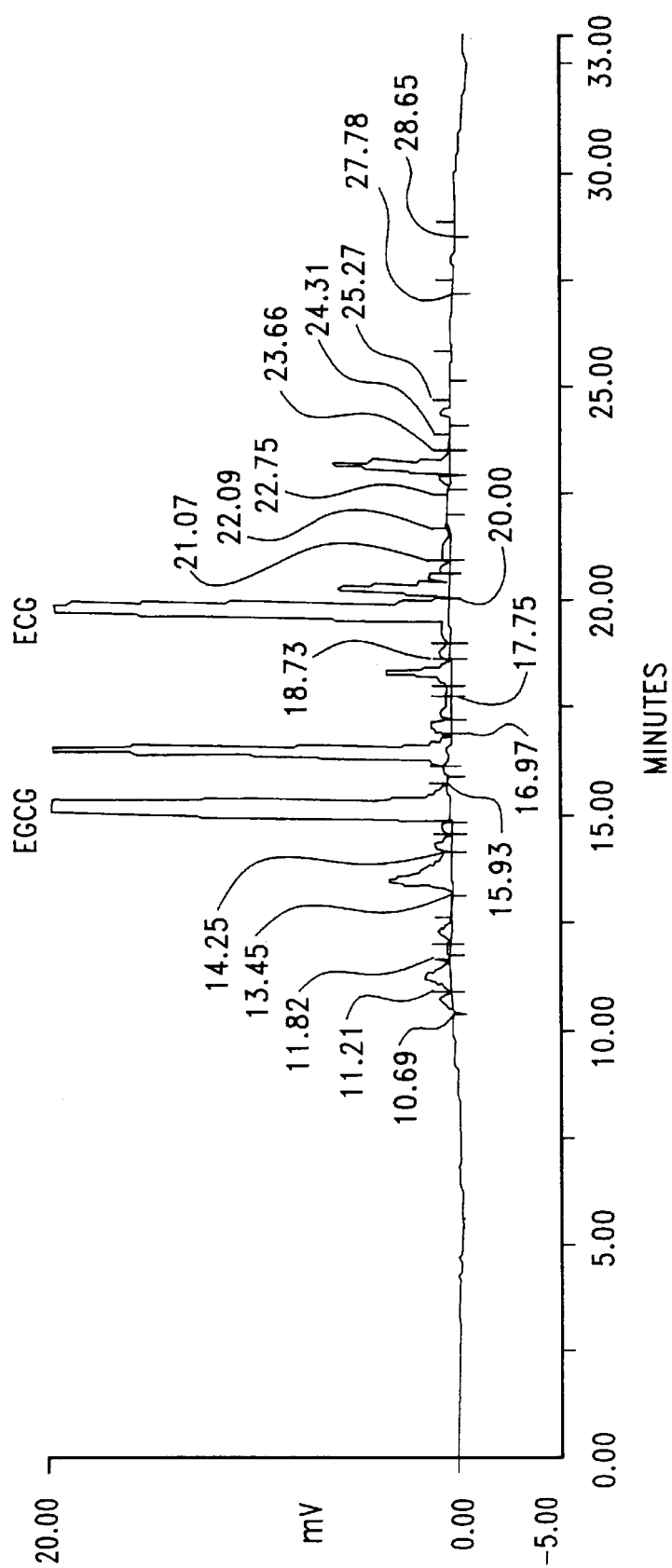
FIG. 3 shows a typical chromatogram of green tea extract after step 2 of the process of the invention.

The preferred second step in the process of the present invention involves loading the caffeine-free mixture of catechins isolated from the first step, discussed above, (i.e., after elution from the first adsorbent with 55% ethanol) onto a second column, preferably a second reverse phase matrix having a second adsorbent specific for catechins. In this step, the preferred second matrix is C-18. In a preferred embodiment of the second step, a substantial portion of the ethanol which may be present in the fractions collected from the first step is removed prior to loading the catechin mixture onto the second column, such that the mixture comprises only about 1–5% residual ethanol. Subsequent to loading the caffeine-free mixture of catechins onto the second adsorbent, selected catechins are desorbed from the adsorbent using 5% food grade (95%) ethanol/water. This step removes a majority of ECG from the catechin mixture. Next, a 12% food grade ethanol/water solution is used to elute the desired catechins to yield a mixture in which the majority of the catechins is EGCG. Small fractions, for example 0.2 column volumes, are collected and pooled after assay by HPLC. In certain instances in which the second step is not performed soon after the first step, it is preferred to store the solution from the first step at slightly acidic pH, preferably by the addition of 0.1% acetic acid. FIG. 3 illustrates a typical chromatogram of a substantially pure, caffeine-free catechin mixture isolated after step two. As shown in FIG. 3, the substantially pure, caffeine-free catechin mixture typically comprises about 85% to 95% EGCG.

The third step in the process of the present invention is to concentrate the substantially pure, caffeine-free catechin mixture isolated from step two, discussed above, prior to performing step four. This mixture comprises approximately 80–90% water and would require a significant amount of time and heat to remove the water from this solution. Heating the solution, particularly over an extended period of time, leads to decomposition of EGCG. Step three of the process of the present invention provides a rapid method of removing the water which requires much less heat and time than would be required to remove water. In step three, the solution from step two is loaded onto a solvent exchange column. In a preferred embodiment, the solvent exchange column comprises a reverse phase matrix, preferably Polyamide CC6 (Machrey-Nagel, (Germany)). After flushing the water off the column, substantially pure caffeine-free EGCG is eluted from the column using 100% methanol, preferably 8 column volumes of methanol, and the methanol fractions are collected and easily evaporated to dryness with little heat.

Figure 4:
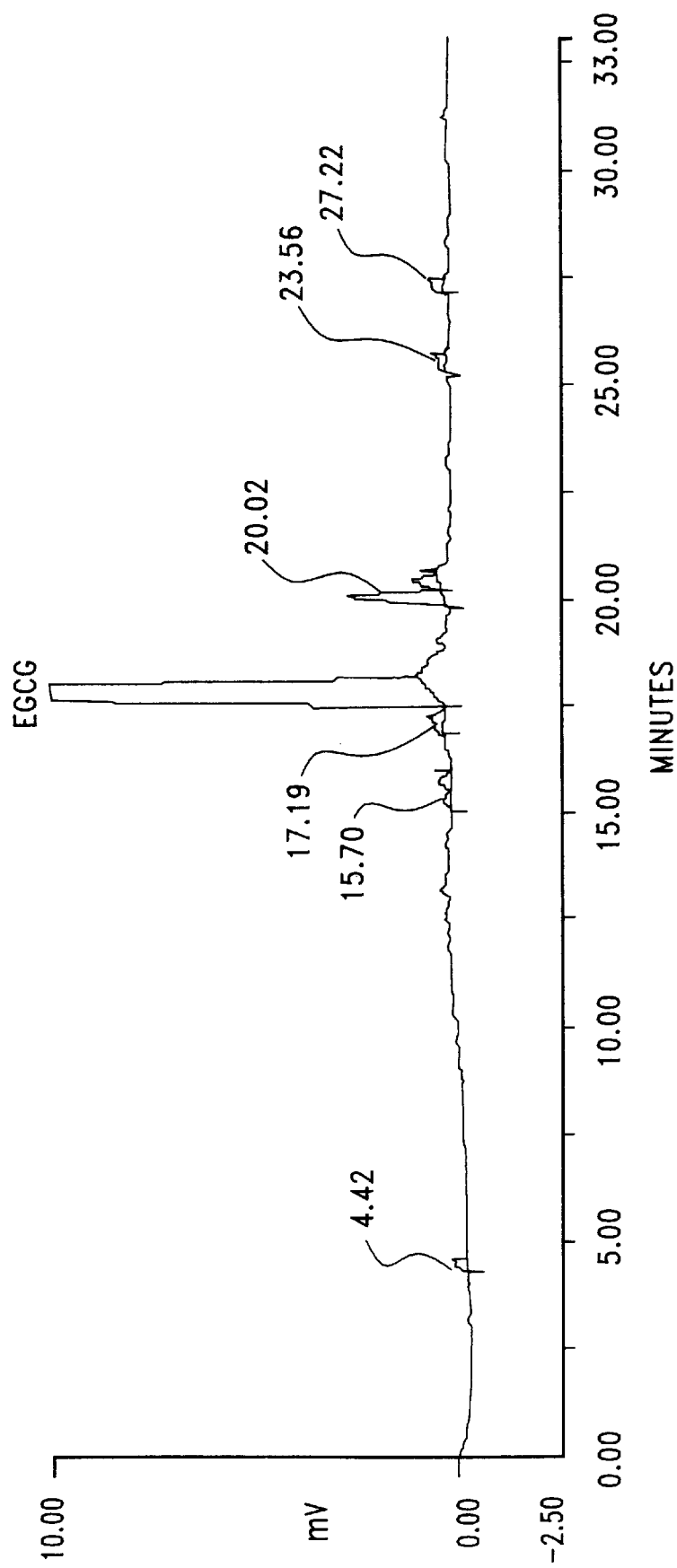
FIG. 4 shows a typical chromatogram of green tea extract after step 4 of the process of the invention.

The preferred fourth and final step in the process is the crystallization or final purification of the caffeine-free catechin mixture from step three, which comprises approximately 88% EGCG. Initially, a crystallization of the EGCG from step 3 was attempted using ethanol/water. However, this method was unsuccessful in isolating crystals of EGCG. Success was achieved in obtaining highly pure crystals of EGCG using methanol/water. Thus, in the fourth step of the method of the invention, the solids from the preceding step are dissolved in a volume of solvent (e.g., 3.27 ml/g). The preferred solvent is 1% methanol/water. In one embodiment, the solids may be dissolved with heat, preferably at 60° C., and optionally the solution is passed through a filter aid such as glass wool. EGCG is crystallized from this solution by refrigerating the solution, preferably at −2° C., for a determined amount of time, preferably overnight. The refrigerated suspension is then passed through a filter. The final product, crystallized EGCG, is optionally washed with ice water followed by 5% EtOH/water to remove any residual color, and then dried. The EGCG isolated after this final step is highly pure. FIG. 4 illustrates a typical chromatogram of the highly pure, caffeine-free EGCG product isolated after the final step in the process of the present invention. This highly pure, caffeine-free EGCG product preferably comprises 95%–98% EGCG and most preferably 98% EGCG. Average isolated recovery of this highly pure EGCG from this step are about 89%. The highly pure, caffeine-free EGCG product may be used in pharmaceutical composition for uses in therapeutics. Even higher purities of EGCG may be obtained by further recrystallizations of the EGCG isolated from step 4 of the process of the invention.

The following non-limited examples provide specific high yield, high purity processes for isolating and purifying catechins from plant tissues. All scientific and technical terms have the meanings as understood by one with ordinary skill in the art. Catechin recovery was assayed using the HPLC method CAT2 and CAT2A (Table 1) using a Hypersil 5-micron C18 column (250×4.6 mm), acetonitrile and 1% citric acid buffer as the solvent system, and a flow rate of 1 mL/minute. Compounds were detected at 274 nm. HPLC was measured on a Hitachi 2000 spectrophotometer. Commercially available chemicals were used without any further purification.

TABLE 1

| CAT2 | | | CAT2A | | |
|---|---|---|---|---|---|
| Time (min) | ACN | Buffer | Time | ACN | Buffer |
| 0.0 | 0 | 100 | 0.0 | 0 | 100 |
| 25.0 | 25 | 75 | 35.0 | 20 | 80 |
| 26 | 0 | 100 | 36.0 | 0 | 100 |
| 30 | 0 | 100 | 40.0 | 0 | 100 |

EXAMPLE 1

Isolation of Caffeine-free Mixed Catechins Comprising 30% EGCG from Green Tea Leaves Extract A reversed phase matrix column (15.24×300 cm, about 55 L/CV) containing Polyamide CC6 (Machrey-Nagel, Germany) was equilibrated with 100% water for 3 column volumes (CV) prior to loading. The column was dry packed and washed with methanol for 4 CV prior to use. (If the column had been used previously, the column was cleaned with 0.38% NaOH or KOH for 6 CV and then washed with 100% water for 10 CV to a pH of 7). Approximately 3500 grams of green tea extract (Thomas J. Lipton) was weighed. This was equal to about 10 g EGCG/L of column media or about 64 g green tea extract/L column media. The solids were dissolved with mixing in about 35L of water, and this solution was pumped onto the Polyamide column. The column was washed with 100% water for 4 CV to remove other waste solids and then eluted with 10% of food grade (95%) ethanol for 8 CV to remove remaining waste solids. The desired catechins were eluted from the column with 100% food grade ethanol for at least 7 CV. All of the 100% ethanol fractions were collected and concentrated to dryness. The solids were dried in a vacuum oven overnight at 25 mm Hg at 30–35° C.

EXAMPLE 2

Isolation of Caffeine-free Mixed Catechins Comprising 80% EGCG/ECG from Green Tea Leaves Extract A Polyamide CC6 column and the green tea leaves extract were prepared as in Example 1 above. The extract was pumped onto the column at about 140 mL/min. The column was washed with 4 CV of 100% water to remove about 45% of the solids along with all of the caffeine. Next, the column was washed with 10% of food grade ethanol/water for 8 CV to remove another 10% solids, which contained gallocatechin (GC), epigallocatechin (EGC) and most of the epicatechin (EC). Alternatively, the column may be washed with a 9.5% solution of food grade ethanol/5% isopropanol in water.

The product was eluted from the column with 55% solution of food grade % ethanol/water for at least 7 CV (alternatively, as 52.25% solution of 3C ethanol in water may be used). The eluent is collected in 0.2 CV fractions. The flow rates ranged from 120–240 mL/min at 30 PSI. The pressure increased with loading and with increased ethanol concentration, necessitating lowering the flow rate for a time. The elution collected was monitored by HPLC, and selected fractions, based on EGCG and ECG purities, were combined and evaporated on a flash evaporator at 100 mTorr vacuum with steam heat and then concentrated to a dry solid on a rotary evaporator at 25 mm Hg at 60° C. The solids were dried overnight in a vacuum oven at 30–35° C. at 35 mm Hg. The recovery was about 65–75% EGCG/ECG and the purity was 78–82%.

EXAMPLE 3

Isolation of Caffeine-free Mixed Catechins Comprising EGCG Having a Purity of 86% from Green Tea Leaves Extract Green tea leaves extract was purified as in Example 2 above, with the exception that all of the fractions from the 55% ethanol elution were combined. The 55% ethanol fractions were partially concentrated to remove the ethanol and then loaded onto a C-18 column at about 9–10 g EGCG per liter of C-18. The column was eluted with 5% ethanol for 9 CV and then 12% ethanol for 7 CV. The EGCG recovery averaged about 88% with purities of about 86%.

EXAMPLE 4

Isolation of Caffeine-free Mixed Catechins Comprising +95% EGCG from Green Tea Leaves Extract Green tea leaves extract was purified as in Example 3. Fractions from the C-18 column containing EGCG were loaded onto a solvent exchange column (Polyamide CC6, Machrey-Nagel), eluted with 100% methanol, and the solvent was removed by rotary evaporation. The solids were then dissolved with heat at 60° C. The solution was then filtered through glass wool to remove any solids. The solution was then chilled to −2° C. overnight. The crystals were filtered through #42 Whatman paper and then washed twice with about 30–50 mls chilled water. The crystals were collected and dried in a vacuum oven overnight at 35° C. The recovery was about 89% with purities of the EGCG of about 95–98%.

The foregoing description is considered as illustrative only of the principles of the invention. Furthermore, since numerous modifications and changes will readily occur to those skilled in the art, it is not desired to limit the invention to the exact construction and process shown as described above. Accordingly, all suitable modifications and equivalents may be resorted to falling within the scope of the invention as defined by the claims which follow.

The embodiments of the invention in which an exclusive property or privilege is claimed are defined as follows:

1. A method for isolating an essentially caffeine-free mixture of catechins comprising about 30% EGCG from any plant material that contains catechins and which may contain caffeine, wherein said mixture of catechins is between about 70–80% pure, said method comprising:
   contacting the plant material for a selected period of time with a solvent wherein at least some of said catechins are soluble and transported into said solvent to form a crude extract;
   loading said crude extract onto a column wherein said column contains an adsorbent for specifically adsorbing said catechins;
   washing said adsorbent with a wash solution, wherein caffeine is removed and wherein said catechins remain adsorbed to said adsorbent; and
   desorbing said catechins from said adsorbent with 100% ethanol, whereby said essentially caffeine-free mixture of catechins is isolated.

2. The method of claim 1, wherein said adsorbent is a reversed phase matrix.

3. The method of claim 2, wherein said reverse phase matrix is polyamide.

4. The method of claim 1, wherein said wash solution comprises water containing between about 0 and 10% ethanol.

5. The method of claim 1 wherein said plant material comprises green tea leaves.

6. A method for isolating an essentially caffeine-free mixture of catechins comprising between about 60–75% EGCG from any plant material that contains catechins and which may contain caffeine, wherein said mixture of catechins is between about 78–82% pure, said method comprising:
   (a) contacting the plant material for a selected period of time with a solvent, wherein at least some of said catechins are soluble and transported into said solvent to form a crude extract;
   (b) loading said crude extract onto a column, wherein said column contains an adsorbent for specifically adsorbing said catechins;
   (c) washing said adsorbent with a wash solution, wherein caffeine is removed and wherein said catechins remain adsorbed to said adsorbent; and
   (d) desorbing said catechins from said adsorbent with 55% ethanol, whereby said essentially caffeine-free mixture of catechins is isolated.

7. The method of claim 6, wherein said adsorbent is a reversed phase matrix.

8. The method of claim 7, wherein said reversed phase matrix is polyamide.

9. The method of claim 7, wherein said plant material comprises green tea leaves.

10. The method of claim 6, wherein said wash solution comprises water containing between about 0–10% ethanol.

11. The method of claim 6, wherein said plant material comprises green tea leaves.

12. A method for isolating an essentially caffeine-free mixture of catechins comprising between about 85–95% EGCG from any plant material that contains catechins and which may contain caffeine, said method comprising:
   (a) contacting the plant material for a selected period of time with a solvent, wherein at least some of said catechins are soluble and transported into said solvent to form a crude extract;
   (b) loading said crude extract onto a first column, wherein said first column contains a first adsorbent for specifically adsorbing said catechins;
   (c) washing said first adsorbent with a wash solution, wherein caffeine is removed and wherein said catechins remain adsorbed to said first adsorbent;
   (d) desorbing said catechins from said first adsorbent with a first eluent comprising 55% ethanol, whereby an essentially caffeine-free mixture of catechins comprising between about 60–75% EGCG is isolated;
   (e) loading said essentially caffeine-free mixture of catechins isolated in step (d) onto a second column, wherein said second column comprises a second adsorbent; and
   (f) eluting said mixture of catechins from said second column with a second and a third eluent, whereby said essentially caffeine-free mixture of catechins comprising between about 85–95% EGCG is isolated.

13. The method of claim 12, wherein said first adsorbent is a reversed phase matrix.

14. The method of claim 13, wherein said reversed phase matrix is polyamide.

15. The method of claim 12, wherein said wash solution comprises water containing between about 0 and 10% ethanol.

16. The method of claim 12, wherein said second eluent comprises 5% EtOH.

17. The method of claim 12, wherein said third eluent comprises 12% EtOH.

18. The method of claim 12 wherein said second adsorbent is a reversed phase matrix.

19. The method of claim 18 wherein said reverse phase matrix is C-18.

20. A method for isolating an essentially caffeine-free mixture of catechins comprising between about 95–98% EGCG from any plant material that contains catechins and which may contain caffeine, said method comprising:
   (a) contacting the plant material for a selected period of time with a solvent, wherein at least some of said catechins are soluble and transported into said solvent to form a crude extract;
   (b) loading said crude extract onto a first column, wherein said first column contains a first adsorbent for specifically adsorbing said catechins;
   (c) washing said first adsorbent with a wash solution, wherein caffeine is removed and wherein said catechins remain adsorbed to said first adsorbent;
   (d) desorbing said catechins from said first adsorbent with a first eluent comprising 55% ethanol, whereby an essentially caffeine-free mixture of catechins comprising between about 60–70% EGCG is isolated;

(e) loading said essentially caffeine-free mixture of catechins isolated in step (d) onto a second column, wherein said second column comprises a second adsorbent;

(f) eluting said essentially caffeine-free mixture of catechins from said second column with a second and a third eluent, whereby an essentially caffeine-free mixture of catechins comprising between about 85–95% EGCG is isolated;

(g) loading said essentially caffeine-free mixture of catechins from step (f) onto a solvent exchange column;

(i) eluting said essentially caffeine-free mixture of catechins from said solvent exchange column with methanol;

(j) removing said methanol from said essentially caffeine-free mixture of catechins eluted in step (i); and (k) crystallizing said essentially caffeine-free mixture of catechins from step (j) after removal of said methanol to yield said essentially caffeine-free mixture of catechins comprising between about 95–98% EGCG.

21. The method of claim 20, wherein said first adsorbent is a reversed phase matrix.

22. The method of claim 21, wherein said reversed phase matrix is polyamide.

23. The method of claim 20, wherein said wash solution comprises water containing between about 0–10% ethanol.

24. The method of claim 20, wherein said second adsorbent is a reversed phase matrix.

25. The method of claim 24, wherein said reversed phase matrix is C-18.

26. The method of claim 20, wherein said second eluent comprises 5% EtOH.

27. The method of claim 20, wherein said third eluent comprises 10% EtOH.

28. The method of claim 20, wherein said plant material comprises green tea leaves.

29. The method of claim 20, wherein said solvent exchange column comprises polyamide.

30. The method of claim 20, wherein said essentially caffeine-free mixture of catechins isolated in step (k) is crystallized from 1% methanol/water.

* * * * *